(12) United States Patent
Hastings et al.

(10) Patent No.: US 6,408,207 B1
(45) Date of Patent: Jun. 18, 2002

(54) HEART STIMULATION DEVICE

(75) Inventors: David Hastings, Lake Oswego, OR (US); Max Schaldach, Erlangen (DE); Gary Rolison, Portland; Robert R. Weyant, Dureham, both of OR (US); Helmut Hutten, Graz (AT)

(73) Assignee: Biotronik Mess-und Therapiegerate GmbH & Co., Berlin (DE)

( * ) Notice: Subject to any disclaimer, the term of this patent is extended or adjusted under 35 U.S.C. 154(b) by 0 days.

(21) Appl. No.: 09/282,650

(22) Filed: Mar. 31, 1999

(30) Foreign Application Priority Data

Mar. 31, 1998 (DE) ......................................... 198 15 540

(51) Int. Cl.⁷ .............................................. A61N 1/365
(52) U.S. Cl. ...................................................... 607/17
(58) Field of Search .............................. 607/17, 18, 19, 607/20

(56) References Cited

U.S. PATENT DOCUMENTS

| | | |
|---|---|---|
| 4,899,752 A | 2/1990 | Cohen |
| 5,143,065 A | 9/1992 | Adkins et al. |
| 5,355,894 A | 10/1994 | Sivard |
| 5,645,575 A | 7/1997 | Stangl et al. |
| 5,730,125 A * | 3/1998 | Prutchi et al. |
| 5,733,312 A * | 3/1998 | Schloss et al. ................ 607/17 |

FOREIGN PATENT DOCUMENTS

| | | |
|---|---|---|
| EP | 770407 A1 | 5/1997 |
| EP | 793978 A2 | 9/1997 |

OTHER PUBLICATIONS

Oct. 11,2000 European Search Report for EP 99 25 0100.

\* cited by examiner

*Primary Examiner*—Scott M. Getzow

(57) ABSTRACT

A device for maintaining or reestablishing a natural heart rhythm by generating an electrical stimulation signal. In particular a device in the form of an implantable heart pacemaker that displays at least one sensor arranged inside the patient's body for picking up a body-specific signal containing information concerning demand for heart performance, or another magnitude relevant to the heart. The device is characterized by the fact that connected downstream to the sensor is a processing unit that obtains from the measurement signal a body-specific rhythm signal whose periodicity is equal to or greater than the periodicity of the breathing activity, and thus lies above the periodicity of the heart activity, whereby the body-specific rhythm signal forms a control signal that influences the stimulation signal.

10 Claims, 1 Drawing Sheet

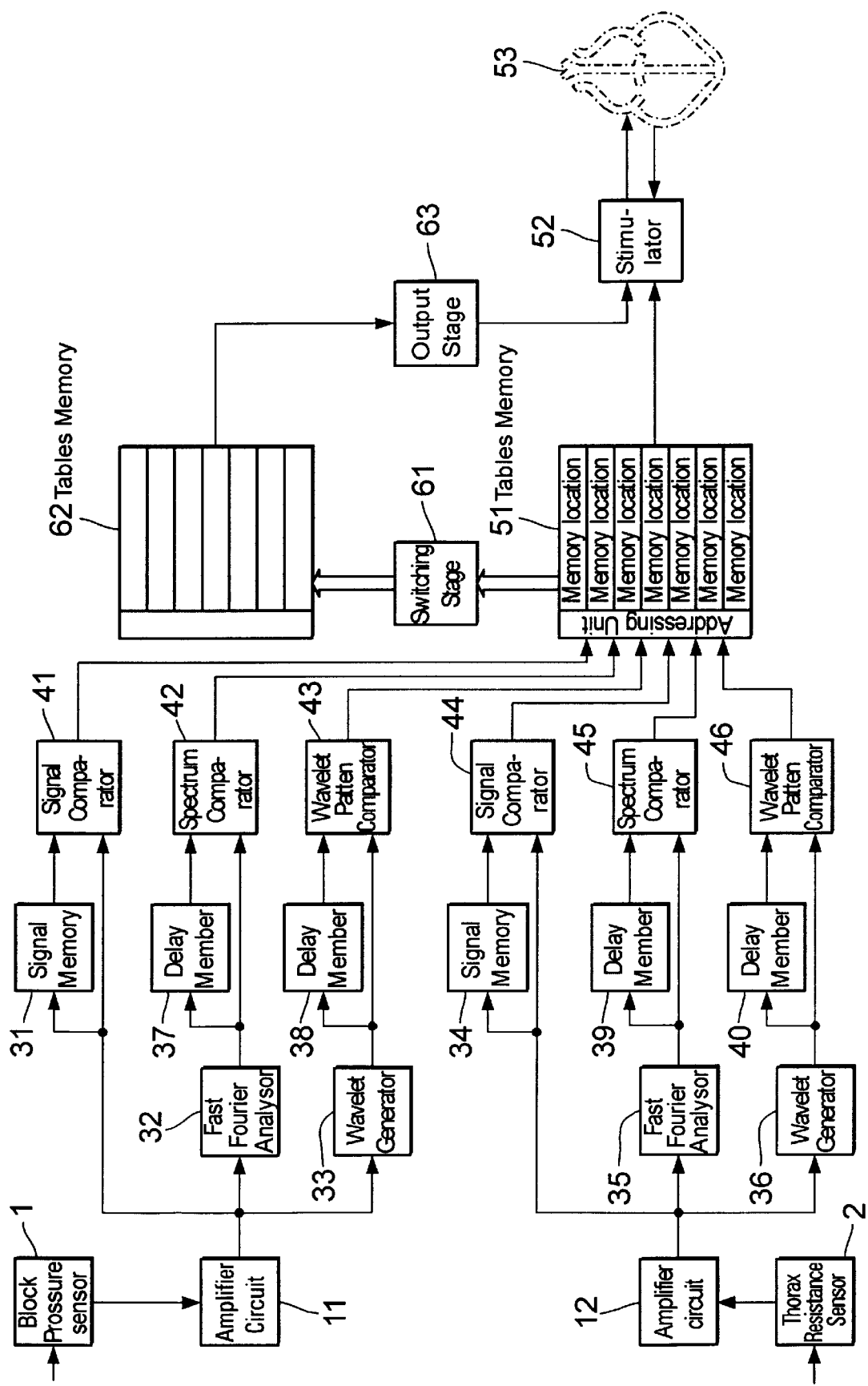

HEART STIMULATION DEVICE

TECHNICAL FIELD

The present invention relates to pacemakers, and more particularly, to pacemakers that pick up body specific signal containing information concerning a demand for hear performance. Known from the prior art are manifold devices that display at least one sensor arranged inside the body of the patient for receiving a body-specific measurement signal containing information concerning demand for heart performance, in order to derive therefrom, among other things, a signal for influencing the stimulation rate.

Devices in existence until now started out from the fact that there exists a direct and time-correct relationship between the change in the body-specific measurement signal containing information concerning demand for heart performance and the stimulation magnitude to be influenced, as for example the amplitude, the rate or the average frequency of occurrence of signals picked up by a sensor, and the heart rate.

However, it has been shown that a direct processing of this type in the time or frequency domain often does not lead to the desired results.

Therefore, the task underlying the invention is to improve the controlling of stimulation events and, more particularly, of the heart rate.

SUMMARY

The task, starting out from a device based on the precharacterizing clause of claim 1, is accomplished by the features given in the characterizing part of claim 1.

The invention includes the technical teaching that in the determination of a magnitude influencing the series of the stimulation signal, also to be observed are those relationships that extend beyond a direct association.

Belonging to this, on the one hand, is a transformation of the time periods to be considered, in such a manner that periodic observation also takes place over past time periods, and that control of the heart rate is checked by the repeated appearance of complex frequency sequences or event sequences that display a specific periodicity or rhythm system. The events themselves are identified by comparison of patterns. The periodicity of the frequency sequences or event sequences here clearly deviates from the natural heart rate, and lies in the range from several seconds up to days or months.

In this manner, it is possible to "decode" a body-specific rhythm system and to make it accessible to the heart stimulation, which rhythm system, to be sure, until now has already played an important role in controlling the vasomotor system of the human body, but could not be used for reconstructing natural heart rhythm.

In the case of the signals to be evaluated, we are dealing with circulation magnitudes whose constant fluctuation in rhythmic variations also contains information concerning demand for heart performance. Here, we are dealing in particular with rhythmic variations of the intra-arterial pressure and/or pressure differences picked up at different measurement points in the vascular system, which pressure differences form a measure for vascular resistance between the measurement points.

In the case of the rhythmic pattern superimposed on the blood pressure, we are dealing with wave trains of different arrangement, which wave trains can be ascertained by their periodicity—and, therewith, via the digital-filter or correlation procedures employed for their detection or by appropriately-matched periodic measurement time-segments, which pick up the current amplitude response and/or the associated frequency pattern.

Associated with the invention is the important advantage that, for the first time, signals that until now were not capable of being detected, or that remained unobserved, co-determine the stimulation rate, so that sensors detecting the physical activity of the patient can be dispensed with.

The use of the device in accordance with the invention for maintaining or reconstructing a natural heart rhythm by generating an electrical stimulation signal relates, in particular, to implantable heart pacemakers for treating bradycardia or tachycardia, as well as rhythm-correcting devices, which are also in use as implantable defibrillators.

If, according to the invention, there is connected to the downstream side of a sensor a processing unit that obtains from the measurement signal a body-specific rhythm signal whose periodicity is at least equal to the periodicity of breathing activity, and thus lies above the periodicity of heart activity, whereby the body-specific rhythm signal forms at least indirectly a control signal that influences the point in time, or the time sequence and/or the point in time, of the stimulation signal, then this means that information is taken from a rhythm signal impressed on the circulation system or the nervous system that is of significance for heart activity. It has been found that these signals are also of significance for the heart activity of man, and a stimulation in correlation to such signals forms at least a physiological supplement to signals that are relevant for heart function and picked up some other way from the patient's body.

One essential application here consists in particular in a stimulation rate adapted to the patient's "internal clock", corresponding to a physiological day-night rhythm. In many cases, however, it is also proves to be favorable if circulation rhythms or other biological rhythms of the patient are followed in the stimulation. A stimulation of this kind, corresponding to a biological rhythm, must not be confused with such "biological rhythms" as are printed out in tables or predicted in purely arbitrary fashion by computers without closer reference to the actual biological object, in the manner of a horoscope.

More rapid body rhythms occurred in a periodicity that begins with the breathing activity and corresponds to an essentially 6- to 20-second rhythm, in particular a 10-second rhythm. However, these rhythms are, mind you, slower than actual heart activity and are preferably in a frequency reduction ratio thereto.

The selection of the body-specific rhythm signal can be appropriately accomplished by means of digital filtering or use of a correlation technique; also, the synchronization of appropriate phase locked loops (PLL) permits a high sensitivity.

In the case of a digital processing, there also exists the possibility of effecting, in advantageous fashion, a detection or a synchronization of periodic or non-periodic processes by comparison of complete signal patterns within the amplitude and/or frequency range. Here, in particular in the processing unit, selected by means of a time window within a time segment of a predetermined duration comprising at least several seconds, is at least one periodically-occurring signal, or a corresponding portion of a signal, having a characteristic amplitude response or frequency pattern, and derived from the sequence of the appearance of this pattern is the body-specific rhythm signal that influences the time sequence or the point in time of the stimulation signal. The width of the time segments to be used in this processing corresponds here, at most, to the period duration of the expected signals or signal portions. A determination of a control signal based on the similarity or accordance of amplitude or frequency patterns appearing in the time segments includes the advantage that a similarity of the signal portions determining the rhythm frequency is recognized more rapidly and more reliably even in the case of less-frequently repeating periods, and the "build up" of filter circuits or the like need not be waited upon in order to detect the periodic signal portions. This is particularly convenient in the case of rhythms with a long repeat time.

In this, for detection of coincident signal patterns, stored in particular is the periodic signal, or a corresponding signal portion having a characteristic amplitude response or frequency pattern appearing in the time segment in each case, whereby the pattern of the current time segment is continuously compared with at least one similar periodically-occurring signal recorded earlier, or with a corresponding signal portion having a characteristic amplitude response or frequency pattern and, in coincidence with the later-appearing, periodically-occurring signal, or corresponding signal portion having a characteristic amplitude response or frequency pattern, a control signal is emitted when the degree of conformity of the patterns to be compared with one another exceeds a predetermined value, whereby derived from the signal indicating the conformity is the control magnitude that influences the magnitude of the stimulation. In place of the frequency pattern, it is also possible here to compare the time response of one or several spectral portions in the frequency pattern that was (were) picked up within a time segment (wavelet).

The control magnitude, which influences the time sequence or the point in time of the stimulation signal, can here also be derived from the rate, the average frequency, the temporal change of the rate, or of its average frequency, of the signal indicating conformity, so that there results a statistical compression of the derived information that is drawn upon for the stimulation. A corresponding compression of the information can also be achieved if the information from the amplitude response pattern and from the spectral pattern is evaluated together.

For generating frequency spectra, the time-dependent signal is appropriately subjected to a Fast-Fourier-Transformation (FFT).

In addition to influencing the control signal for control of the time sequence of the stimulation signal by periodic influences, it can also be advantageous to vary the control signal and therewith the stimulation signal by means of a positive or negative random signal. The stimulation frequency of the pacemaker will, therefore, not be set so as to be completely fixed, rather will be varied about the desired frequency value. Even in the healthy human body, the heart rate is subjected to more or less random fluctuations that can have various causes. Such fluctuations should therefore also be capable of being reproduced in a pacemaker. If a relatively low random value is superimposed on the control signal, then also hereby a possible positive feedback coupling in the control circuit can be prevented. If a relatively high random value is superimposed on the control signal, it is then possible hereby to "feel one's way toward" the hemodynamic loading limit, in which case it is then necessary to ascertain the effects of the variations on a measurement magnitude located in the hemodynamic control circuit. By the varying of the stimulation frequency, it is also possible to determine other variables of the hemodynamic control circuit such as time constants and proportionality of the control magnitudes, which, in turn, can be used for optimizing the parameters of the rate-adaptation algorithm of the pacemaker.

In order to counteract a possible tendency to oscillation of circulation functions within the patient's body by a phase-synchronous excitation because of the generated heart stimulation, it is useful if means are provided that, upon determination of an excessive rise in the amplitude of the current temporal mean value of the body-specific rhythm signal in comparison to a preceding long-term mean value, change the phase position of the change of the stimulation magnitude, in relation to the course of the temporal change of the determined body rhythm magnitudes, by a predetermined or statistically-determined phase angle.

Coming into consideration as body-specific sensor signals that are subjected to the processing in accordance with the invention are, in particular, periodic portions of the intracardial electrogram, the intracardial or transthoracic impedance, blood temperature, vagal/parasympathetic or baroreceptive nerve signals, intra-arterial pressure or the difference in pressure picked up at two different measurement locations as the peripheral vessel resistance of the parts of the circulation system located between the measurement locations, or the electrochemical cellular ion potential.

Other advantageous developments of the invention are characterized in the dependent claims or are represented in more detail in the following with the aid of the figures, together with the description of the preferred implementation of the invention.

DESCRIPTION OF THE DRAWINGS

FIG. 1 is a block diagram of a pacemaker embodying the present invention.

DETAILED DESCRIPTION

In the implementation example represented in the FIGURE, we are dealing with a device for maintaining or reconstructing a natural heart rhythm by generating an electrical stimulation signal, in the form of an implantable pacemaker that displays at least one sensor arranged inside the patient's body for receiving a body-specific signal containing information concerning demand for heart performance, or some other heart-relevant magnitude.

In this, connected downstream of the sensors 1 and 2 is a processing unit consisting of several elements to be described in the following, which processing unit obtains from the measurement signals supplied to these sensors (represented by input arrows) a body-specific rhythm signal whose periodicity comprises at least a few seconds. The period for the signals can, e.g., lie within the breathing range or above. In any event, it lies above the periodicity of the heart activity. The body-specific rhythm signal forms at least indirectly a control signal that influences the point in time, or the time sequence and/or the point in time, of the stimulation signal.

In the case of sensor 1, it should be a matter of a blood pressure sensor, and in the case of sensor 2 of a measuring device for the thorax resistance, which device, in conventional design, is formed through the two electrodes of a unipolar heart stimulation electrode (one pole forms the electrode installed inside the heart, while the counter pole is formed by the stimulator housing inside the chest cavity).

However, also coming into consideration as input signals are the intracardial electrogram, the intracardial or transthoracic impedance, blood temperature, vagal/parasympathetic or baroreceptive nerve signals, intra-arterial pressure or the pressure difference picked up at two different measurement locations, the electrochemical cellular ionic potential, or others.

For this, the selection of the body-specific rhythm signal takes place in the components in the top part of the figure, within a frequency range that essentially corresponds to the day/night rhythm, and thus to the inner human clock. On the other hand, there takes place in the lower part of the figure a selection of the body-intrinsic rhythm within the range of the breathing frequency or a fraction of the breathing frequency, i.e. within a frequency region which essentially corresponds to a 6- to 20-second rhythm, in particular a 10-second rhythm.

In the drawing, provided in blocks 11 and 12 are amplifier circuits for the signals picked up by the sensors. Stored in blocks 31 and 34 in storage components is the amplitude response determined in each case over a time segment of the sensor signal. In blocks 41 and 44 there takes place, for the respective signals within a time window adapted to the rhythm system of the signal, a determination of conformity with the current signal, which likewise consists of a selected amplitude response within a time segment. With conformity established, the time interval is determined and further processed as a signal that is characteristic of the rhythm system.

Undertaken in stages 32 and 35 is a Fast Fourier Analysis, so that serving as a signal pattern for the comparison, in stages 42 and 45 respectively, of the signal currently appearing with a signal that is time-delayed in a delay member 37 or 39 respectively, is the average frequency spectrum in the respective time segment.

Instead of this, in stages 33 and 36 wavelets are generated and—after a delay in delay members 38, 40—are likewise compared with one another in stages 43 and 46, so that a conclusion can be reached concerning the periodicity of the corresponding sensor signal.

Here, selected and retained in the processing unit within a time segment of predetermined duration, comprising at least several seconds, is at least one periodically appearing signal or a corresponding signal portion having a characteristic amplitude response or frequency pattern.

The periodically-occurring signal picked up in each case in the time segment, or a corresponding signal portion having a characteristic amplitude response or frequency pattern, is stored in the subsequent stages, the current time segment is continually compared with at least one similar, previously-picked-up, periodically-occurring signal, or a corresponding signal portion having a characteristic amplitude response or frequency pattern, and a control signal is emitted in coincidence with the later-appearing, periodically-occurring signal, or a corresponding signal portion having a characteristic amplitude response, when the degree of conformity of the patterns to be compared with one another exceeds a predetermined value. The periodicity of the rhythmic signals thus results from the signal delaying of successive signals, which is necessary for causing these signals (whether they are the amplitude response or the spectrum) to coincide with their predecessors according to a similarity or correlation process.

The output signals from stages 41 to 46 therefore represent the periodicity determined in each case by the kind of processing means 31 to 46 of the rhythmic signal portions detected in the input signals by sensors 1 and 2. By addressing a subsequent memory formed as a reference table, the combination of the output signals of stages 41 to 46 occurs, which are representative of the periodicity of the signals, as addressing signals for the memory, which, in turn, sends the control sequences stored at the addressed locations in the memory to the conventional heart pacemaker or defibrillator. Here, it is a matter of a rate control signal or a unique signal for triggering an individual tachycardia-terminating or defibrillation sequence.

It can be seen that through the combination of the output signals of stages 41 to 46 complex evaluations of the body-rhythmic signals can be undertaken. For this, coming into consideration in particular are their logical operations, overlays, time derivations, accumulation values, etc.

The contents of the addressed memory locations of the tables memory 51 emit an output signal to the otherwise-conventional, controllable stimulator part 52, which, in known manner, is in interaction with the heart 53. In the case of a rate-controlled pacemaker, the basic rate is influenced by the control signals from the output of memory 51, while in the case of a defibrillator a defibrillation cycle is executed whenever the body rhythm signals exceed a predetermined threshold value.

Additionally to the generation of a body-specific rhythm signal for influencing the control signal that influences the point in time and/or the time sequence of the stimulation signal, it is also appropriate to superimpose an additional positive or negative random value on the control signal. This is based on the knowledge that even in the healthy human body the heart rate is subjected to random variations. These variations can, in part, have origins in the breathing activity, so that, e.g. in the case of intensive breathing activity, the phase position of heart contractions is, as a rule, determined by the breathing activity, not, however, by its average frequency. Known also is so-called respiratory arrhythmia, which expresses itself in such a way that heart rate increases briefly upon inhaling and, on the other hand, decreases during exhaling. Other causes for such variations are, for example, to be seen in the cooperation of the sympathetic and parasympathetic nervous system or in the cooperation of the heart frequency and the vasomotor system.

Since the healthy heart displays random variations of heart frequency, it is to be presumed that this behavior is physiologically or, more particularly, hemodynamically advantageous, so that, for this reason, this behavior also should be reproduced by the pacemaker.

Therefore, if the correcting magnitude is not controlled statically, then, as a rule, a more rapid and more flexible response to the measured magnitude is to be expected, which, in turn, can lead to a more a more rapid and more flexible accommodation to the correcting magnitude. The randomly-occurring variations acting together can lead to the accelerated detection of favorable control circuit conditions.

Until now it was assumed that a relatively low random value is superimposed on the control signal. However, if relatively high random values are superimposed, there then exists the possibility to "feel one's way toward" hemodynamic loading limits. In doing this, it is necessary to ascertain the effects of the variations on a measurement magnitude located in the hemodynamic control circuit, for example on the stroke volume represented by the intracardial impedance. For example, by a strong increase or decrease of the stimulation frequency, the stroke volume, by means of which the circulation system seeks to equalize the variation of heart rate, it brought to its upper or lower control limit. In the case of ischemia-endangered patients, upon reaching the control limit the stimulation frequency simultaneously represents a measure for the upper limit frequency, which for avoiding ischemias should not be reached. Other diagnostic procedures besides recognition of ischemia limits are likewise conceivable on the basis of control limits that are reached by the variation in stimulation frequency. By variation of the stimulation frequency, also capable of being determined are other magnitudes of the hemodynamic control circuit, such as time constants and proportionality of the control magnitudes, which in turn can be used for optimizing the parameters of the rate-adaptation algorithm of the pacemaker.

Since with this device we are dealing with one in which a body-specific rhythm magnitude that influences the stimulation of the heart can itself again be influenced by body-internal coupling, there can exist—as with any control system—the danger of a tendency to oscillation. Therefore, to avoid this, means are planned that, in the case of an excessive increase of the average amplitude, implement appropriate counter measures for the circuit-rhythm characteristic magnitude. Used by stages 41 to 46 for this is not only the characteristic time interval of the consecutive pattern signals for the internal circuit rhythm in each case, but also their average amplitude for addressing the tables memory 51. If this amplitude exceeds a predetermined maximum value, then addressed via a switching stage 61 is another tables memory 62, which effects, via an output stage 63, a change of the stimulation magnitude in proportion to the course of the temporal change of the ascertained body rhythm about a predetermined or a statistically-determined phase angle.

The invention is not limited in its implementation to the preferred implementation example given above. To the contrary, a number of variants are possible that make use of the represented solution in implementations of fundamentally different types.

What is claimed is:

1. Device for maintaining or reestablishing a natural heart rhythm by generating an electrical stimulation signal, in particular a device in the form of an implantable heart pacemaker that displays at least one sensor arranged inside the patient's body for picking up a body-specific signal containing information concerning demand for heart performance, or another magnitude relevant to the heart, characterized by the fact that:

connected downstream to the sensor is a processing unit that obtains from the measurement signal a body-specific rhythm signal whose periodicity is equal to or greater than the periodicity of the breathing activity, and thus lies above the periodicity of the heart activity, whereby the body-specific rhythm signal forms a control signal that influences the stimulation signal; and selected in the processing unit within a time segment of a predetermined duration and comprising at least several seconds is at least one periodically-appearing signal or a corresponding signal portion having a characteristic amplitude response or frequency pattern, and that the body-specific rhythm is derived from the succession of the appearance of this pattern, which body-specific rhythm influences the time sequence and/or the point in time of the stimulation signal, the sequential time segments displaying a predetermined interval that corresponds to the expected perodicity of the rhythm.

2. Device according to claim 1, characterized by the fact that the periodically-occurring signal picked up in each case in the time segment, or the corresponding signal portion having a characteristic amplitude response or frequency pattern, is stored, that the current time segment is continually compared with at least one similar, previously-picked-up, periodically-occurring signal, or a corresponding signal portion having a characteristic amplitude response or frequency pattern, and that, in coincidence with the later-appearing signal, a signal is emitted that indicates the time difference of appearance when the degree of conformity of the patterns to be compared with one another exceeds a predetermined value, whereby generated in particular from the signal indicating the time difference is the body-specific rhythm signal.

3. Device according to claim 1, characterized by the fact that instead of the frequency pattern, the temporal courses of one or several spectral portions in the frequency pattern are compared.

4. Device according to claim 3, characterized by the fact that the body-specific rhythm signal is derived from the temporal change of the signal indicating the time difference.

5. Device according to claim 1, characterized by the fact that the frequency pattern is subjected to a Fast-Fourier-Transformation (FFT).

6. Device for maintaining or reestablishing a natural heart rhythm by generating an electrical stimulation signal, in particular a device in the form of an implantable heart pacemaker that displays at least one sensor arranged inside the patient's body for picking up a body-specific signal containing information concerning demand for heart performance, or another magnitude relevant to the heart, characterized by the fact that connected downstream to the sensor is a processing unit that obtains from the measurement signal a body-specific rhythm signal whose periodicity is equal to or greater than the periodicity of the breathing activity, and thus lies above the periodicity of the heart activity, whereby the body-specific rhythm signal forms a control signal that influences the stimulation signal and is generated from the superimposition or accumulation of several from among the rate, the average frequency, the temporal change of the rate or its average frequency, of the signal indicating conformity, for at least two time segments of different duration.

7. Device according to claim 1, characterized by the fact that the control magnitude that influences the point in time of the stimulation signal is generated by the superimposition or accumulation of several from among the rate, the average frequency, the temporal change of the rate or its average frequency, of the signal indicating conformity, for at least two time segments of different duration, during which is evaluated the amplitude response and the course of the frequency pattern.

8. Device for maintaining or reestablishing a natural heart rhythm by generating an electrical stimulation signal, in particular a device in the form of an implantable heart pacemaker that displays at least one sensor arranged inside the patient's body for picking up a body-specific signal containing information concerning demand for heart performance, or another magnitude relevant to the hear, characterized by the fact that connected downstream to the sensor is a processing unit that obtains from the measurement signal a body-specific rhythm signal whose periodicity is equal to or greater than the periodicity of the breathing activity, and thus lies above the periodicity of the heart activity, whereby the body-specific rhythm signal forms a control signal that influences the stimulation signal, and superimposed on the control signal, which influences the time sequence or the point in time of the stimulation signal, is an additional positive or negative random value.

9. Device according to claim 8, characterized by the fact that a relatively small random value is superimposed.

10. Device according to claim 8, characterized by the fact that a relatively large random value is superimposed.

* * * * *